(12) United States Patent
Chang et al.

(10) Patent No.: US 6,974,553 B2
(45) Date of Patent: Dec. 13, 2005

(54) POLYTHIAETHER COMPOUNDS AND THEIR USE AS CORROSION INHIBITORS

(75) Inventors: Zen-Yu Chang, North Wales, PA (US); Liliana Minevski, The Woodlands, TX (US); Ping Lue, Boothwyn, PA (US)

(73) Assignee: GE Betz, Inc., Trevose, PA (US)

( * ) Notice: Subject to any disclaimer, the term of this patent is extended or adjusted under 35 U.S.C. 154(b) by 439 days.

(21) Appl. No.: 10/272,128

(22) Filed: Oct. 15, 2002

(65) Prior Publication Data

US 2004/0076542 A1 Apr. 22, 2004

(51) Int. Cl.$^7$ .......................... C23F 11/00; C07C 55/00; C07C 353/00
(52) U.S. Cl. .......................... 252/395; 422/7; 562/594; 564/501; 568/46
(58) Field of Search .............................. 252/395; 422/7; 562/594; 564/501; 568/46

(56) References Cited

U.S. PATENT DOCUMENTS

| | | | |
|---|---|---|---|
| 4,744,948 A | * | 5/1988 | Incorvia .......................... 422/7 |
| 6,147,225 A | | 11/2000 | Gaboury et al. |
| 6,187,227 B1 | | 2/2001 | Minevski et al. |

* cited by examiner

*Primary Examiner*—Paul A. Zucker
(74) *Attorney, Agent, or Firm*—Duane Morris LLP

(57) ABSTRACT

The corrosion of metals in contact with aqueous alkanolamine solutions in acid gas removal units is inhibited by adding to the alkanolamine solution a corrosion inhibiting amount of a polythiaether compound.

6 Claims, No Drawings

POLYTHIAETHER COMPOUNDS AND THEIR USE AS CORROSION INHIBITORS

FIELD OF THE INVENTION

The present invention relates to polythiaether compounds and to methods of inhibiting corrosion of metals in contact with aqueous alkanolamine solutions in acid gas removal amine units using polythiaether compounds.

BACKGROUND OF THE INVENTION

The conditioning of naturally occurring liquid and gas streams by absorbing acid gases such as $CO_2$ and $H_2S$ in an absorbent solution is a well known commercial practice. Acid gas removal is commonly practiced in the oil refining, natural gas recovery, ammonia plant and wood pulp industries. For example, when crude oil and natural gas are removed from a formation they frequently contain $CO_2$ or $H_2S$ (acid gases). Acid gases are removed from the hydrocarbon in an acid gas removal amine system (amine unit). Amine units are typically constructed of carbon steel and operate at temperatures of from about 110° to about 300° F., at pressures of from about 10 to about 500 psig and with less than about 10 ppm of oxygen present as an undesirable contaminant in the aqueous alkanolamine solution. An amine unit utilizes an alkanolamine such as monoethanolamine (MEA), diethanolamine (DEA), methyldiethanolamine (MDEA), diisopropylamine (DIPA), and diglycolamine (DGA) in an aqueous solution. The hydrocarbon containing acid gases are contacted with the aqueous amine solution in a tray or packed absorber where the amine reacts with the acid gases, thereby removing them from the hydrocarbon and forming an aqueous amine solution containing the absorbed acid gases (rich stream). The amine-acid gas reaction is later reversed in a plate or packed stripper resulting in an acid gas stream and a reusable amine solution (lean stream).

Amine units present a variety of corrosion control problems. Unreacted carbon dioxide dissolved in the aqueous alkanolamine solution forms acid species which are corrosive to metals. Oxygen can enter an amine unit through storage tanks, sumps, surge vessels, and the like and attack metals, causing corrosion. Oxygen also can oxidize the alkanolamine. Oxidation and degradation products of alkanolamines can cause metal corrosion. Efforts to control corrosion in amine units usually focus on the use of metallurgy, minimization of acid gas flashing, filtration, stress relieving, process controls and corrosion inhibitors such as metal passivating agents. However, environmental and safety concerns have limited the practicality of using some materials such as nickel, cobalt, calcium, copper, chromium, zinc, tin, aluminum, magnesium and cyano compounds and the like as corrosion inhibiting agents. Since corrosion, if left untreated, can cause shutdown of an amine unit, corrosion control is a very important consideration. In addition, most corrosion control efforts have focused on treating the rich stream of the amine unit. However, the lean sections of amine units also experience corrosion.

Therefore, a need exists for compositions which when added to an aqueous alkanolamine solution in an acid gas removal amine unit inhibit corrosion of metals in contact with the aqueous alkanolamine solutions and which are effective for inhibiting corrosion in both the rich and lean portions of the amine unit.

Accordingly, it is an object of the present invention to provide compounds for inhibiting corrosion of metals in contact with aqueous alkanolamine solutions.

It is an additional object of the present invention to provide aqueous acid gas removal solutions for use in amine units which are inhibited against acid gas promoted corrosion of metals.

It is yet another object of this invention to provide a method for inhibiting corrosion of metals in contact with aqueous alkanolamine solutions in amine acid gas removal units.

SUMMARY OF THE INVENTION

To achieve the foregoing objects, the present invention provides compositions for inhibiting corrosion of metals in contact with aqueous alkanolamine solutions. The compositions are polythiaether compounds having from 2 to about 12 sulfur atoms on each of the "open" crown rings which are effective for inhibiting corrosion in alkanolamine acid gas removal systems. Unless specified otherwise, the term "polythiaether compound(s)" is used herein to mean polythiaether compounds and/or their salts with mineral acids.

The invention also provides aqueous acid gas removal solutions which are inhibited against acid gas promoted corrosion of metals. The solutions are comprised of polythiaether compounds in aqueous alkanolamine solutions.

The invention further provides a method for inhibiting corrosion of metals in contact with aqueous alkanolamine solutions. The method comprises adding an amount of polythiaether compound to an aqueous alkanolamine solution, sufficient to establish a concentration of polythiaether compound in the aqueous solution which is effective for the purpose of inhibiting metal corrosion in an amine acid gas removal unit.

DESCRIPTION OF THE PREFERRED EMBODIMENTS

In accordance with the present invention, a composition and a method for inhibiting corrosion of metals in contact with aqueous alkanolamine solutions is provided. The present inventors have discovered that one or more polythiaether compounds, when added to an aqueous alkanolamine solution, significantly inhibits corrosion of ferrous metals in contact with the alkanolamine solution. In addition, the inventors have discovered that polythiaether compounds of this invention are effective for inhibiting metal corrosion in both the rich and lean portions of aqueous alkanolamine unit acid gas removal equipment. Also in accordance with the present invention, a composition and a method for inhibiting corrosion of metals in contact with hydrocarbons that contain sufficient separated aqueous phase and dissolved acid gases to cause corrosion is provided. The aqueous phase may contain salts such as alkaline or alkaline earth chlorides. The acid gas is typically $CO_2$ or $H_2S$. The hydrocarbon is typically crude oil resulting from production, but may be lighter refined streams. The present inventors have discovered that one or more polythiaether compounds, when added to the hydrocarbon containing the separate aqueous phase and acid gas, significantly inhibits corrosion of ferrous metals in contact with the hydrocarbon fluid. The polythiaether compounds have the formula shown as follows:

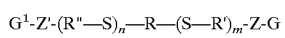

and their appropriate salts with mineral acids, wherein n=1–10;
m=1–10;
R is C2–C12 linear or branched alkyl; aryl optionally substituted with C1–C6 alkyl, halogen, C1–C4 alkoxy, $NR^3R^4$, phenyl, nitro, cyano, $COOR^3$, $OCOR^4$ wherein $R^3$, $R^4$ are independently H, C1–C4 alkyl, phenyl; C4–C10 heterocyclic; C7–C10 alkylaryl; or C—[(CH$_2$)—]$_4$, provided that when R is C—[(CH$_2$)—]$_4$, each of the four CH$_2$ is independently bonded through the S atom to the same or different —(S—R')$_m$-Z-G or $G^1$-Z'-(R"—S)$_n$— groups;

R' and R" are independently C2–C12 linear or branched alkyl; aryl optionally substituted with C1–C6 alkyl, halogen, C1–C4 alkoxy, $NR^3R^4$, phenyl, nitro, cyano, $COOR^3$, $OCOR^4$ wherein $R^3$, $R^4$ are independently H, C1–C4 alkyl, phenyl; C4–C10 heterocyclic; C7–C10 alkylaryl;

Z and Z' are independently S, O, $NR^5$, $COR^6$;

G and $G^1$ are independently H; methyl; R'; R"; (CH$_2$CH$_2$NH)$_r$H, wherein r=0–100;

$R^5$=H; C1–C8 alkyl; (CH$_2$CH$_2$NH)$_r$H, r=0–100;

$R^6$=$NR^3R^4$; $OR^7$ wherein $R^7$=H, C1–C4 alkyl, phenyl; and OM wherein M=Na, Li, K;

and when Z=$NR^5$, G or $G^1$ and $R^5$ together with nitrogen can also form cyclic amines comprising piperazines, morpholines, or piperidines.

Compounds that can be obtained by reacting dihaloalkanes or dihalo derivatives of polythiaether with polyetheramines, alkylenepolyamines other than polyethyleneimines, hydroxyalkyl(poly)amines, hydrazines and hydroxylamines are also expected to have similar corrosion inhibition activities.

Exemplary dihalo derivatives include, but are not limited to, dichloropropane, dibromopropane, pentaerythrityl tetrabromide, 1,9-dichloro-3,7-dithianonane, 1,15-dichloro-3,6,10,13-tetrathiapentadecane (TPD), and 2,16-dichloro-4,7,11,14-tetrathiaheptadecane. Exemplary polyamines include, but are not limited to, pentaethylenehexamine, tetraethylenepentamine, triethylenetetramine, diethylenetriamine, and ethylenediamine. Polyetheramines include, but are not limited to, RO(CH$_2$CH$_2$O)$_n$CH$_2$CH$_2$CH$_2$NH$_2$ wherein R is a C1–C4 alkyl. Hydroxyalkyl(poly)amines include, but are not limited to, ethanolamine, diethanolamine, -(3-aminopropyl) diethanolamine, and N-(3-aminopropyl) diisopropanolamine.

Note that it is also expected that oligomers containing more than one polythia unit in the products could be generated when utilizing multifunctional amines in reaction with dihalo derivatives.

It is further anticipated that the polythiaether compounds of the present invention may be blended with polyamines, e.g., polyalkyleneamines such as diethylenetriamine (DETA), triethylenetetramine (TETA), and tetraethylenepentamine (TEPA) as an effective corrosion inhibitor.

The following examples describe manufacturing procedures for a preferred embodiment of the present invention.

EXAMPLE 1

Synthesis of 3,7-dithianonane-1,9-diol

One hundred seventy grams of sodium hydroxide was mixed with 1000 mL of ethanol. While stirring, the mixture was heated to 83° C. to dissolve sodium hydroxide. Heat was turned off and 440 g of 2-mercaptoethanol was added through an additional funnel. To the resulting solution was added 1,3-dibromopropane in such a rate to maintain a gentle reflux without external heating. The resulting slurry was heated at 78° C. for 3 hours. Solid sodium bromide was filtered off and the ethanol solution was distilled under 1 atm to remove most of ethanol, and then under vacuum to remove residual ethanol. The resultant suspension was filtered again to remove solid sodium bromide, to give 392 g of the diol as a liquid.

EXAMPLE 2

Synthesis of 1,9-dichloro-3,7-dithianonane

A dilute sodium hydroxide solution scrubber was set up to absorb the hydrogen chloride and sulfur dioxide gases produced from this reaction. A 39.3 g sample of 3,7-dithianonane-1,9-diol from Example 1 was mixed with 40 mL of hexane. The two immiscible layers were vigorously stirred while 47.6 g of thionyl chloride was added dropwise at room temperature. The reaction temperature went up to 37° C. after about half of thionyl chloride was added and then cooled down. External heat was provided while the rest of thionyl chloride was added to maintain the temperature at 33° C. The resulting suspension was stirred for one hour after the addition was complete. A 1.5 g amount of ethanol was added to destroy any excess of thionyl chloride that might remain. Hexane was then removed by normal distillation followed by vacuum distillation, to give 45.7 g of the dichloride as a liquid.

EXAMPLE 3

Synthesis of 3,6,10,13-tetrathiapentadecane-1,15-diol

A solution of sodium salt of 2-mercaptoethanol was made by mixing 16.2 g of sodium hydroxide in 72 mL of ethanol with 31.6 g of 2-mercaptoethanol. The above solution was then added through an additional funnel to 49.1 g of 1,9-dichloro-3,7-dithianonane from Example 2. The exothermic reaction kept the reaction refluxing during the addition. A 20.4 g amount of ethanol was used to rinse the funnel. The resulting slurry suspension was stirred at the refluxing temperature for 1.5 hours. While hot, solid sodium chloride was filtered off and washed with 47.5 g of ethanol. Ethanol was removed from the filtrate by distillation under nitrogen at 1 atm and then under vacuum to give 63.2 g of the diol as a liquid, which solidified upon cooling.

EXAMPLE 4

Synthesis of 1,15-dichloro-3,6,10,13-tetrathiapentadecane

A dilute sodium hydroxide solution scrubber was set up to absorb the hydrogen chloride and sulfur dioxide gases produced from this reaction. A 55.6 g amount of 3,6,10,13-tetrathiapentadecane-1,15-diol from Example 3 was melted at 62° C. and mixed with 32 mL of toluene. To the suspension was added 42.6 g of thionyl chloride dropwise. The reaction was exothermic while the first half amount of thionyl chloride was added. External heating was provided for the remaining addition period to maintain the temperature at 50° C. A 1.5 g amount of ethanol was added to destroy any of excess thionyl chloride. Toluene was removed under vacuum distillation to give 63.2 g of the dichloride product as a brown liquid, which solidified upon cooling.

EXAMPLE 5

Synthesis of Reaction Product between tetraethylenepentamine and 1,15-dichloro-3,6,10,13-tetrathiapentadecane A 6.8 g amount of 1,15-dichloro-3,6,10,13-tetrathiapentadecane was suspended in 65.5 g of ethylene glycol. A 7.3 g amount of tetraethylenepentamine was added to the suspension in 2 minutes while stirring at room temperature. The heat from the exothermic reaction took the temperature to 30° C. The resulting solution was stirred at 78° C. for 6 hours. The reaction mixture was filtered to remove a small amount of brown solid, to give 75.6 g of a solution.

In the testing of the present invention, eight polythiaether compounds were evaluated. These are:

Formula I

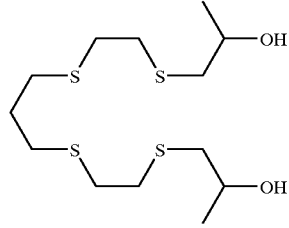

Formula II

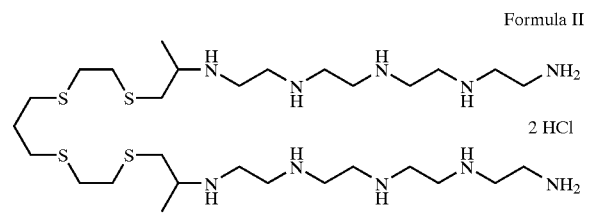

2 HCl

Formula III

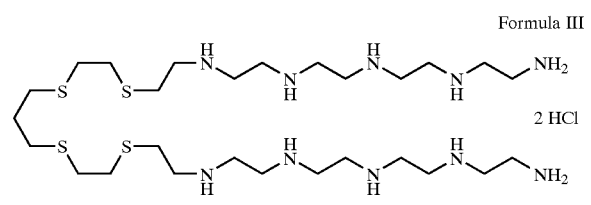

2 HCl

Formula IV

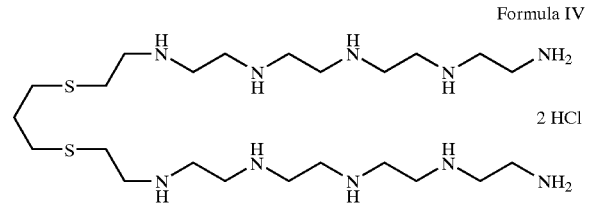

2 HCl

Formula V

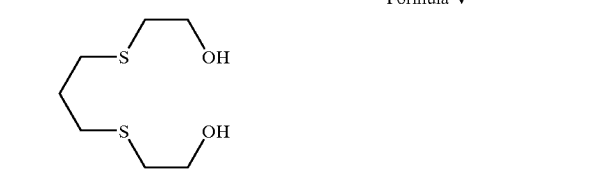

Formula VI

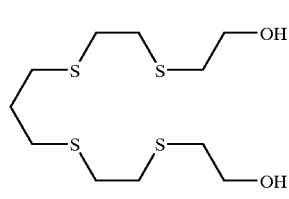

Formula VII

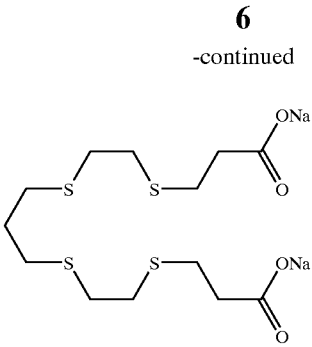

Formula VIII

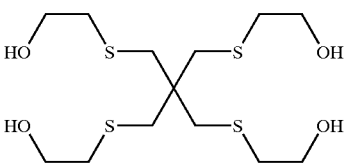

The extent of corrosion inhibition was obtained by performing electrochemical experiments in glass cells in the absence and presence of the above inhibitors. Mild steel electrodes in the form of a cylinder were used as the metal of investigation. Tests were conducted at 79° C. Testing conditions were those simulating rich streams (systems purged with $CO_2$) of alkanolamine units. Diethanolamine (DEA) and monoethanolamine (MEA) were used as the test fluids. Besides the corrosive gases, additional contaminants found in amine systems were introduced into the test fluids. The composition of the DEA and MEA fluids used for testing is shown below:

| DEA Solution | MEA Solution |
| --- | --- |
| 30 wt % DERA | 25 wt % MEA |
| 960 ppm NaCl | 700 ppm formic acid |
| 50 ppm $Na_2SO_4$ | 100 ppm acetic acid |
| 110 ppm formic acid | 1 ppm NaCl |
| 50 ppm acetic acid | |
| 50 ppm propionic acid | |
| 130 ppm glycolic acid | |

Test results (% protection) are shown in Tables 1 and 2.

TABLE 1

Inhibition (% Protection) from electrochemical measurements in 30 wt % DEA sparged with $CO_2$

| Treatment | Concentration (ppm) | % Protection | Test Duration (hrs) |
| --- | --- | --- | --- |
| Formula I | 10 | 93 | 15 |
| Formula I | 10 | 85 | 7 |
| Formula II | 10 | 87 | 18 |
| Formula II | 20 | 96 | 18 |
| Formula II | 10 | 93 | 17 |
| Formula III | 10 | 88 | 23 |
| Formula IV | 10 | 25 | 23 |
| Formula V | 20 | 40 | 23 |
| Formula VI | 10 | 92 | 23 |

TABLE 2

Inhibition (% Protection) from electrochemical measurements in 25 wt % MEA sparged with $CO_2$

| Treatment | Concentration (ppm) | % Protection | Test Duration (hrs) |
|---|---|---|---|
| Formula I | 10 | 99 | 15 |
| Formula I | 10 | 94 | 7 |
| Formula II | 10 | 95 | 18 |
| Formula III | 20 | 83 | 25 |
| Formula V | 20 | 40 | 25 |
| Formula V | 20 | 50 | 25 |
| Formula VI | 20 | 96 | 25 |
| Formula VII | 10 | 77 | 50 |
| Formula VIII | 10 | 83 | 50 |

The inventors also believe that since the polythiaether compounds can form strong complexes with transition metal ions, they can be used for a broad range of applications in water and process treatments, and can be used as catalysts for phase transfer reactions, as encapsulating materials for electronic devices, as corrosion inhibitors and as components of electrorheological fluid, etc. Particularly, the novel polythiaether compounds of this invention are expected to be useful as metal ion chelating and complexing agents, as corrosion inhibitors for cooling towers and boilers, $CO_2$ enhanced oil recovery systems and crude unit overhead, as influent water and wastewater treatments, as corrosion inhibitors in electronic packages, as metal extraction materials for mining processes and as metal surface treatments. In addition, depending on the ionic charge, structure and properties of the polymer used during synthesis of the polythiaether compounds, the polythiaether compounds of this invention are expected to be useful as dispersants, coagulants, flocculants, or film forming agents.

In addition to the various alkanolamine solutions, the open chain TEPA compounds have been tested as corrosion inhibitors for the crude unit overhead and oilfield pipeline applications.

Relative to crude unit overhead, weight loss corrosion rate evaluations were performed using a high velocity autoclave. Tests performed in these autoclaves simulated conditions present near typical water dewpoints and were conducted at 200° F. with a mixture of 95% deaerated synthetic overhead naphtha and 5% synthetic dewpoint water. The synthetic dewpoint water contained 1100 ppm HCl, 130 ppm $H_2SO_3$, 730 ppm $H_2SO_4$, 120 ppm acetic acid, 150 ppm propionic acid, 125 ppm butyric acid, 200 ppm pentanoic acid, 60 ppm hexanoic acid, 250 ppm $H_2S$, 160 ppm $NH_3$ and neutralized with an amine solution until reaching a pH of approximately 5. In these tests, a coupon assembly was utilized which could generate linear velocities of 40 ft/s at the coupon's outer edge by attaching the coupons to a stirring shaft rotated at 3000 rpm. TPD-TEPA was tested at 20 ppm active and gave 67% corrosion inhibition.

Relative to oilfield pipeline corrosion, tests were conducted by a standard three electrode electrochemical method with a 1018 carbon steel working electrode, glassy carbon counter electrode, and a Silver/Silver Chloride reference. Tests were run at 100° F. in a 1-liter custom-made glass vessel. The ratio of water (NACE brine) to hydrocarbon (kerosene) was 90 to 10. The brine composition was 9.82% NaCl, 0.404% $CaCl_2*2H_2O$, 0.186% $MgCl_2*6H_2O$. The fluids were continually sparged with $CO_2$.

Test results for various open chain materials are shown in the Table 3, below. The majority of these results were at least comparable to present treatment approaches.

TABLE 3

| Treatment | Ppm | % Protection |
|---|---|---|
| Formula I | 10 | 75 |
| Formula II | 2.5 | 87 |
| Formula II | 5 | 97 |
| Formula II | 10 | 100 |
| Formula III | 2.5 | 35 |
| Formula III | 5 | 84 |
| Formula III | 5 | 86 |
| Formula III | 7.5 | 93 |
| Formula VI | 5 | 70 |
| Formula VI | 5 | 94 |
| Formula VI | 10 | 100 |
| Formula VI | 15 | 100 |

While this invention has been described with respect to particular embodiments thereof, it is apparent that numerous other forms and modifications of this invention will be obvious to those skilled in the art The appended claims and this invention generally should be construed to cover all such obvious forms and modifications which are within the true spirit and scope of the present invention.

What is claimed is:

1. A method of inhibiting corrosion of metals in contact with an aqueous alkanolamine solution in an acid gas removal amine unit comprising adding to the aqueous alkanolamine solution an effective corrosion inhibiting amount of a polythiaether compound having the formula:

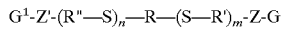

$$G^1\text{-}Z'\text{-}(R''\text{—}S)_n\text{—}R\text{—}(S\text{—}R')_m\text{-}Z\text{-}G$$

and their appropriate salts with mineral acids,
wherein n=1–10; m=1–10;
R is C2–C12 linear or branched alkyl; aryl optionally substituted with C1–C6 alkyl, halogen, C1–C4 alkoxy, $NR^3R^4$, phenyl, nitro, cyano, $COOR^3$, $OCOR^4$ wherein $R^3$, $R^4$ are independently H, C1–C4 alkyl, phenyl; C4–C10 heterocyclic; C7–C10 alkylaryl; or C—[$(CH_2)$—$]_4$, provided that when R is C—[$(CH_2)$—$]_4$, each of the four $CH_2$ is independently bonded through the S atom to the same or different —(S—R')$_m$-Z-G or $G^1$-Z'-(R''—S)$_n$— groups;
R' and R'' are independently C2–C12 linear or branched alkyl; aryl optionally substituted with C1–C6 alkyl, halogen, C1–C4 alkoxy, $NR^3R^4$, phenyl, nitro, cyano, $COOR^3$, $OCOR^4$ wherein $R^3$, $R^4$ are independently H, C1–C4 alkyl, phenyl; C4–C10 heterocyclic; C7–C10 alkylaryl;
Z and Z' are independently S, O, $NR^5$, $COR^6$;
G and $G^1$ are independently H; methyl; R'; R''; $(CH_2CH_2NH)_rH$, wherein r=0–100;
$R^5$=H; C1–C8 alkyl; $(CH_2CH_2NH)_rH$, r=0–100;
$R^6$=$NR^3R^4$; $OR^7$ wherein $R^7$=H, C1–C4 alkyl, phenyl; OM wherein M=Na, Li, K;
and when Z=$NR^5$, G or $G^1$ and $R^5$ together with nitrogen form cyclic amines comprising piperazines, morpholines, or piperidines.

2. The method as recited in claim 1, wherein Z and Z' are independently $NR^5$.

3. The method as recited in claim 1, wherein G and G' are independently H, $(CH_2CH_2NH)_rH$, wherein r=0–100 and $R^5$=$(CH_2CH_2NH)_rH$, wherein r=0–100.

4. The method as recited in claim 1, wherein r=1–6.

5. The method as recited in claim 1, wherein the polythiaether compound is further combined with a polyamine selected from the group consisting of diethyleneamine, triethyleneamine, tetraethyleneamine and pentaethylenehexamine.

6. A method for inhibiting metal corrosion in contact with a hydrocarbon containing an amount of a separated aqueous phase and an acid gas to cause corrosion, comprising adding to the hydrocarbon or the aqueous phase an effective corrosion inhibiting amount of a polythiaether compound having the formula:

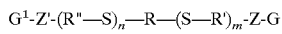

$$G^1\text{-}Z'\text{-}(R''\text{—}S)_n\text{—}R\text{—}(S\text{—}R')_m\text{-}Z\text{-}G$$

and their appropriate salts with mineral acids, wherein n=1–10; m=1–10;

R is C2–C12 linear or branched alkyl; aryl optionally substituted with C1–C6 alkyl, halogen, C1–C4 alkoxy, $NR^3R^4$, phenyl, nitro, cyano, $COOR^3$, $OCOR^4$ wherein $R^3$, $R^4$ are independently H, C1–C4 alkyl, phenyl; C4–C10 heterocyclic; C7–C10 alkylaryl; or C13 [$(CH_2)$—]$_4$, provided that when R is C—[$(CH_2)$—]$_4$, each of the four $CH_2$ is independently bonded through the S atom to the same or different —(S—R')$_m$-Z-G or $G^1$-Z'-(R''—S)$_n$— groups;

R' and R'' are independently C2–C12 linear or branched alkyl; aryl optionally substituted with C1–C6 alkyl, halogen, C1–C4 alkoxy, $NR^3R^4$, phenyl, nitro, cyano, $COOR^3$, $OCOR^4$ wherein $R^3$, $R^4$ are independently H, C1–C4 alkyl, phenyl; C4–C10 heterocyclic; C7–C10 alkylaryl;

Z and Z' are independently S, O, $NR^5$, $COR^6$;

G and $G^1$ are independently H; methyl; R'; R''; $(CH_2CH_2NH)_rH$, wherein r=0–100;

$R^5$=H; C1–C8 alkyl; $(CH_2CH_2NH)_rH$, r=0–100;

$R^6$=$NR^3R^4$; $OR^7$ wherein $R^7$=H, C1–C4 alkyl, phenyl; OM wherein M=Na, Li, K;

and when Z=$NR^5$, G or $G^1$ and $R^5$ together with nitrogen form cyclic amines comprising piperazines, morpholines, or piperidines.

* * * * *

UNITED STATES PATENT AND TRADEMARK OFFICE
CERTIFICATE OF CORRECTION

PATENT NO. : 6,974,553 B2  Page 1 of 1
APPLICATION NO. : 10/272128
DATED : December 13, 2005
INVENTOR(S) : Zen-Yu Chang, Liliana Minevski and Ping Lue It is certified that error appears in the above-identified patent and that said Letters Patent is hereby corrected as shown below:

Column 8, lines 65-66, delete "diethyleneamine, triethyleneamine, tetraethyleneamine" and insert --diethylenetriamine, triethylenetetramine, tetraethylenepentamine-- therefor.

Signed and Sealed this

First Day of April, 2008

JON W. DUDAS
*Director of the United States Patent and Trademark Office*